United States Patent [19]

Taylor et al.

[11] Patent Number: 4,871,463
[45] Date of Patent: Oct. 3, 1989

[54] VERTICAL REACTION VESSEL

[75] Inventors: Michael A. Taylor, Encinitas; Timothy Rogler-Brown, Cardiff By-The-Sea, both of Calif.

[73] Assignee: Sepratech, Carlsbad, Calif.

[21] Appl. No.: 235,375

[22] Filed: Aug. 23, 1988

[51] Int. Cl.⁴ .................................................. E01D 23/10
[52] U.S. Cl. .................................. 210/161; 210/263; 210/351
[58] Field of Search ............... 210/351, 660, 661, 662, 210/663, 670, 681, 263, 291

[56] References Cited

U.S. PATENT DOCUMENTS 3,965,000  6/1976  Milule et al. .................... 210/351

Primary Examiner—Frank Sever
Attorney, Agent, or Firm—Seed and Berry

[57] ABSTRACT

A method and apparatus for uniformly distributing fluid across the entire cross section of a reaction medium and for compensating for volumetric changes in the reaction medium utilized a resilient membrane which cooperates with an adjacent fluid manifold distribution chamber. The combined operation of the manifold distribution chamber with the resilient membrane provides a low resistance to fluid flow in a direction transverse to fluid flow through the reaction medium and a higher resistance to fluid flow across the membrane in the direction of fluid flow through the reaction medium. In this way, fluid is evenly distributed across the cross section of the reaction medium prior to entering the reaction medium and after leaving the reaction medium. The resilient membranes have reserve expansion capabilities, when hydrated, to accommodate expansion in the reaction medium. The resilient membranes are also sufficiently resilient to accommodate expansion of the reaction medium when necessary.

19 Claims, 2 Drawing Sheets

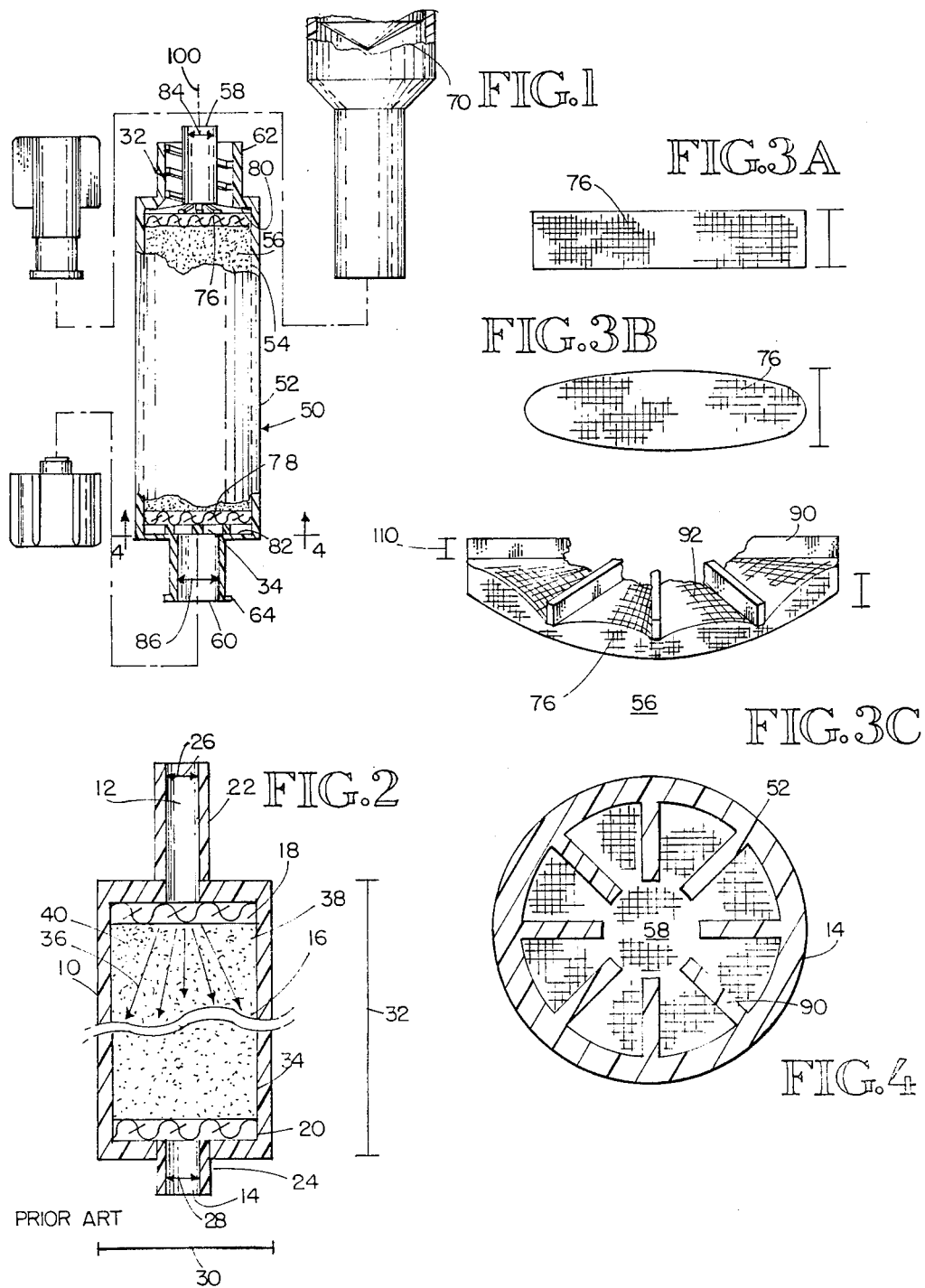

VERTICAL REACTION VESSEL

TECHNICAL FIELD

The invention relates to mechanical structures for vertical reaction vessels. More specifically, the invention relates to apparatus and methods for uniformly distributing fluid through a reaction vessel and for maintaining the viability of a reaction medium contained in the reaction vessel.

BACKGROUND ART

The advance of medical technology has permitted the development of monoclonal antibodies which have been designed with a high degree of affinity for specific cell tissue. These antibodies can be conjugated ("tagged") with radioactive isotopes for the visualization of tissues for which the antibodies are specific. For example, cancer tissue-specific monoclonal antibodies can be conjugated with radioactive isotopes to facilitate imaging of soft tissue turmors which would otherwise be difficult to image with conventional X-ray techniques. In addition, these antibodies can be tagged with radioactive material for the treatment of cancer. This form of chemotherapy is advantageous in that the radioactive material is delivered directly to the site of the tumor through the bloodstream.

Prior to introduction of the above-described site-specific medicine into the human body, the conjugated antibody must be isolated from a reaction solution containing: the desired antibody conjugated with the radioactive material; unbound antibody; unbound radioactive material; and other impurities. Each of these items (other than the desired conjugated antibody) exists as ions in the solution. Thus, the desired, conjugated antibody is typically isolated by passing the reaction solution through an ion-exchange column.

A conventional, prior art, ion-exchange column is identified by reference numeral 10 in FIG. 2. The ion-exchange column has a fluid inlet 12 for introduction of the reaction solution from which the conjugated antibody is to be isolated. The isolated, conjugated antibody exits the ion-exchange column through a fluid outlet 14. The ion-exchange column contains an ion-exchange resin 16 which has an affinity for the anionic, unconjugated radioactive material so as to retain this undesirable material in the ion-exchange column while allowing the uncharged, conjugated antibody to pass therethrough. During this process, other, undesirable anions are retained in the column (during this reaction, the ion-exchange resin gives up a harmless anion, such as chlorine, which exits the fluid outlet 14 with the isolated, conjugated antibody).

The ion-exchange resin 16 typically comprises a polymer material which binds quaternary amino ethyl crystals (such as QAE-Sephadex) together. Prior to introduction of the reaction solution into the fluid inlet 12, the ion-exchange resin 16 is hydrated with a buffer solution. The buffer solution maintains a relatively narrow pH range within the ion-exchange column during passage of the reaction solution therethrough.

Without the buffer solution, the ion-exchange resin was the consistency of a tacky powder. Upon introduction of the buffer solution into the fluid inlet 12, the ion-exchange resin assumes the consistency of a slurry. To prevent the partially liquefied ion-exchange resin from passing through the fluid outlet 14 during operation of the column, and to prevent the tacky, unhydrated ion-exchange resin from falling out the fluid inlet 12 during storage of the ion-exchange column, hard fibrous inserts or "frits" 18, 20 are positioned adjacent to the fluid inlet 12 and fluid outlet 14, respectively.

The insert 20 adjacent to the outlet 14 also traps fine particles which result from degradation of the ion-exchange resin itself. The ion-exchange resin is in the form of a crystalline solid before hydration, and is in the form of a crystalline solid in solution when hydrated. The solid particles of the ion-exchange resin are relatively fragile and swell or contract by osmotic action according to the pH of the buffer solution introduced through the fluid inlet 12. It is highly desirable for all of the solution entering the fluid inlet 12 to fully contact the ion-exchange resin 16 before leaving the fluid outlet 14. Therefore, the ion-exchange resin is relatively tightly packed into the ion-exchange column between the hard inserts 18, 20 to minimize the formation of voids and fluid channels in the reaction medium during operation of the ion-exchange column. As a consequence of this tight packaging and the repeated expansion of the crystals against the hard inserts 18, 20, the crystals begin to fracture and form fine particles ("fines"). These "fines" are trapped in the insert 20 and do not exit the fluid outlet 14. The insert 20 may eventually become clogged with these fine particles diminishing the efficacy of the column even though the ion exchange medium remains functional. In addition, undesirable voids are formed in the ion exchange resin when the resin contracts. Therefore, a need exists for a vertical reaction vessel which can accommodate volumetric changes of an ion-exchange resin contained therein.

In addition to the inability of the prior art ion-exchange column to compensate for volumetric changes in the ion-exchange resin, fluid flow distribution irregularities are associated with this device. As shown in FIG. 2, the fluid inlet 12 and fluid outlet 14 are provided with conventional Luer locks 22 and 24, respectively, having internal diameters 26, 28 which are limited by the outer diameter of a standard Luer lock. The diameter 30 and length 32 of a reaction chamber 34 containing the ion-exchange resin 16 are determined by the desired flow rate of the reaction solution through the ion-exchange column.

As is often the case, the diameter 30 of the reaction chamber 34 is significantly larger than the inner diameters 26, 28 of the fluid inlet and outlet to accommodate a desired flow rate through the ion-exchange resin 16. The reaction solution tends to form a conical fluid distribution 36, as shown in FIG. 2, which does not provide a desired, uniform fluid flow across the entire cross-sectional area of the reaction chamber. A uniform fluid flow is necessary to provide a uniform exposure for all of the reaction fluid flowing through the column. In the conical distribution 36 shown in FIG. 2, the fluid on the outside of the conical distribution has a longer travel path through the ion-exchange resin 16 and a greater period of exposure to the ion-exchange resin than does fluid passing through the center of the distribution. In addition, circled areas 38 and 40 of the ion-exchange resin receive little, if any, fluid flow and thus do not react with the reaction solution. Therefore, a need exists for a vertical reaction vessel which promotes a uniform fluid flow throughout the entire cross section of the ion-exchange resin.

SUMMARY OF THE INVENTION

It is an object of the present invention to provide a vertical reaction vessel which accommodates volumetric changes in a reaction medium contained in a reaction chamber.

It is also an object of the present invention to achieve the above object while providing for a uniform fluid flow through the reaction chamber.

The invention achieves these objects, and other objects and advantages which will become apparent from the description which follows, by providing a vertical reaction vessel with manifold distribution chambers above and below the reaction medium and resilient inserts which expand and contract to accommodate volumetric changes in the reaction medium.

A preferred embodiment of the invention includes an ion-exchange column having a body which partially confines a reaction medium in a reaction chamber. The body has a fluid inlet and a fluid outlet substantially smaller in cross-sectional area than the reaction chamber. Adjacent to the fluid inlet and fluid outlet are manifold fluid distribution chambers which distribute fluid from the fluid inlet and to the fluid outlet throughout the entire cross section of the reaction chamber. Resilient membranes, adjacent to the manifold fluid distribution chambers, prevent the reaction medium from exiting the body through either the fluid inlet or fluid outlet. The resilient membranes expand when hydrated and have sufficient reserve expansion capacity to fill up any gaps or voids which form when the reaction medium contracts. The resilient membranes also have sufficient resiliency to cushion the reaction medium when the reaction medium expands.

The invention also comprises a method for compensating for volumetric changes in a reaction medium and a method for distributing a solution across the entire cross-sectional area of a reaction medium.

BRIEF DESCRIPTION OF THE DRAWINGS

FIG. 1 is a sectional, elevational view of an ion-exchange column employing the manifold distribution chambers and resilient membranes of the present invention.

FIG. 2 is a partial, sectional, elevational view of a prior art ion-exchange column.

FIGS. 3a through 3c are schematic representations of the resilient membranes of the present invention. FIG. 3a shows the thickness of the membrane when unhydrated. FIG. 3b shows the thickness of the membrane when hydrated. FIG. 3c shows the hydrated thickness of the resilient membrane when positioned between the fluid distribution manifold and the ion-exchange resin in the ion-exchange column.

FIG. 4 is a sectional view taken along line 4—4 of FIG. 1.

Figure 6:
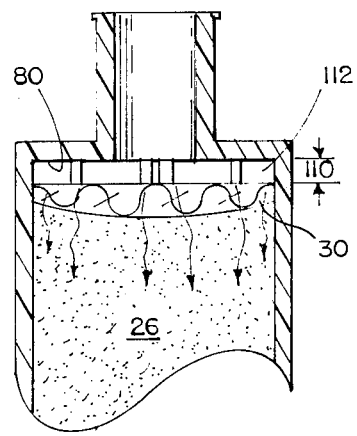
FIG. 6 is an enlarged, sectional, elevational view of the inlet end of the ion-exchange column.

Best Mode for Carrying Out the Invention

A preferred embodiment of an ion-exchange column in accordance with the present invention is generally indicated at reference numeral 50 in FIG. 1. The column has a hollow cylindrical body 52 which defines a receptacle 54 for a reaction medium 56. The column has a fluid inlet 58 and a fluid outlet 60 at opposing ends thereof. The fluid inlet and fluid outlet have female 62 and male 64 Luer locks of the conventional design.

The reaction medium 56 can be any type of reaction medium. However, the preferred embodiment of the invention is most advantageously designed for use with an ion-exchange medium, such as quaternary amino ethyl Sephadex (QAE-Sephadex) or a diethyl aminoethyl Sephadex (DEAE-Sephadex) electrolyte. These materials have the consistency of tacky crystals when dry and of a slurry when hydrated with a buffer solution. This reaction medium is effective in removing electrically charged impurities from a reaction solution (e.g., sodium pertechnetate, technetium dioxide and the hydrolyzed—i.e., carboxylate—form of chelate). All of these impurities exist as anions and are retained on the positively charged (cation) quaternary of the ion-exchange column. The anion of the reaction medium is then expelled through the fluid outlet with any uncharged material, which is thereby isolated from the reaction solution.

As shown in FIG. 1, a reaction solution containing an electrically neutral antibody conjugate of interest and the negatively charged impurities is introduced into the fluid inlet 58 by a syringe 70. Prior to introduction of the reaction fluid into the ion-exchange column 50, a buffer solution is introduced into the reaction medium 56 through the fluid inlet 58 to hydrolyze the reaction medium. As is well known, the individual crystals of the reaction medium expand or contract through osmotic action according to the pH of the buffer solution. To prevent the crystals from fracturing and to prevent the reaction medium from falling out through the fluid inlet and fluid outlets when the reaction medium is dry, resilient membranes 76, 78 are positioned adjacent inlet and outlet ends 80, 82 containing the reaction medium therebetween.

Figure 5:
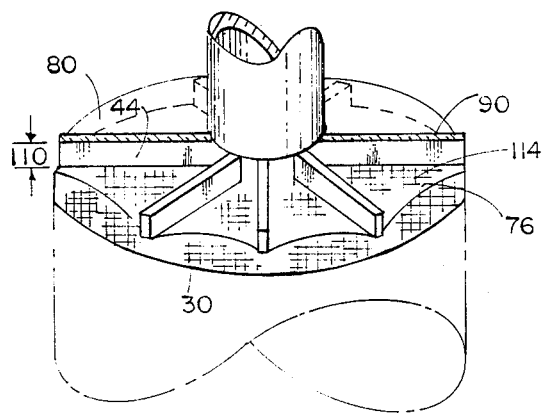
FIG. 5 is an enlarged, sectional, isometric view of the manifold distribution chamber adjacent to the inlet.

As shown in FIG. 3a, the reaction medium has an unhydrolyzed thickness of approximately 0.090 inch. When hydrolyzed, such as with a buffer solution, the medium will expand to a thickness of approximately 0.150 inch, if unrestrained. As shown in FIGS. 3c and 5, the reaction medium is, however, constrained between radially extending fins 90 and the reaction medium 56 so that in areas 92 between the fins the resilient membrane 76 expands to a thickness of approximately 0.110 inch. At the position of the fins 90, the resilient membrane is compressed to a lesser thickness. Thus, the resilient membrane has the capacity to expand towards the reaction medium a distance of approximately 0.040 inch at either end of the reaction chamber 54 to compensate for contraction of the ion-exchange resin if the pH of the buffer solution is relatively large. Conversely, the resilient membranes have the capability to compress approximately 0.020 inch at each end of the reaction chamber when the ion-exchange resin 16 expands if the pH of the buffer solution is low. Thus, fragmentation of the reaction medium is avoided and formation of fines which would tend to clog the resilient membrane 78 near the outlet end 82 of the ion-exchange column, is discouraged.

The resilient nature of the resilient membranes 76, 78 is also effective in providing a radial seating force against the receptacle 54 which holds the membranes in place during wet sterilization procedure.

The fluid inlet 58 and fluid outlet 60 have respective inner diameters 84, 86 which are limited by the standard outer dimensions of the conventional Luer locks. The reaction receptacle 54 has a substantially constant diameter which is significantly larger than these inner diameters so as to provide a satisfactory flow rate of reaction solution through the ion-exchange column. A flow rate of 10 milliliters solution per minute is considered acceptable.

To promote a uniform distribution of fluid from the fluid inlet to the fluid outlet across the entire cross section of the reaction medium, the inlet and outlet ends 80, 82 of the ion-exchange column are provided with the radially extending fins 90. As shown in FIGS. 5 and 6, the fins cooperate with the resilient membrane 76, 78 to form manifold distribution chambers for the reaction fluid.

The resilient membranes 76, 78 provide a relatively high resistance to fluid flow in the direction of the axis 100 of the ion-exchange column 50. As shown in FIGS. 4 and 5, the fins 90 extend radially from the fluid inlet 58 and fluid outlet 60 and have a height 110 sufficient to provide a gap 112 between ends of the reaction chambers 80, 82 and the resilient membranes 76, 78 so as to form radial fluid passageways therebetween. These passageways extend from the fluid inlet to the perimeter of the reaction chamber at the inlet end of the ion-exchange column, and from the perimeter of the reaction chamber to the fluid outlet at the outlet end of the ion-exchange column. The fluid passageways have a relatively low resistance to fluid flow in the radial direction as compared to fluid flow through the resilient membranes in the axial direction. Thus, the passageways cooperate with the resilient membranes to act as fluid distribution manifolds. The manifold adjacent the inlet end 80 of the ion-exchange column 50 distributes fluid evenly across the entire cross section of the reaction chamber when the reaction fluid enters the fluid inlet. The manifold adjacent to the outlet end 82 of the ion-exchange column collects fluid from the entire cross section of the reaction chamber before the fluid exits the fluid outlet.

Any suitably porous, resilient membrane exhibiting the characteristics shown in FIGS. 3a through 3c is suitable for use as the resilient membranes 76, 78 in the ion-exchange column 50 of the present invention. The preferred material is a rolled and pressed cellulose depth filter; and appropriate item is grade 01AP cellulose manufactured by Cuno, Inc., Meriden, Conn.

Other versions and embodiments of the invention are contemplated. For example, as shown in FIG. 5, the fluid passageways generally indicated at reference numeral 114 are defined by the radial pattern of the fins 90 and the swollen shape of the resilient membrane 76. Other fluid passageway shapes are possible which can also achieve uniform fluid distribution over the cross-sectional area of the reaction chamber. Therefore, the invention is not to be limited by the above description but is to be determined in scope by the claims which follow.

We claim:

1. A vertical reaction vessel having a uniform fluid flow design, comprising:
   a body defining a reaction medium receptacle having a receptacle cross-sectional area;
   a reaction medium in the receptacle;
   a fluid inlet and a fluid outlet each communicating with the reaction medium receptacle and each having inlet and outlet cross-sectional areas substantially smaller than the receptacle cross-sectional area;
   manifold chambers adjacent to the fluid inlet and the fluid outlet having manifold cross-sectional areas substantially equal to the receptacle cross-sectional area to provide fluid pathways from the fluid inlet, across the receptacle cross-sectional area and to the fluid outlet; and
   fluid-permeable back pressures means, located between the manifold chambers and the reaction medium, for gently compensating for volumetric changes of said reaction medium and for evenly distributing fluid through the fluid pathways to encourage substantially uniform fluid flow through the reaction medium.

2. The reaction vessel of claim 1 wherein the manifold chambers include a plurality of fins extending radially outward from the fluid inlet and fluid outlet to position the fluid back pressure means in a spaced relationship from the fluid inlet and fluid outlet so as to define the fluid pathways.

3. The reaction vessel of claim 1 wherein the fluid-permeable back pressure means includes resilient membranes which expand when hydrated and wherein the reaction medium is relatively fragile and has a volume which expands and contracts according to the ionic strength of a buffer solution introduced into the fluid inlet, whereby the volume of the resilient membranes change to complement volume changes of the reaction medium to prevent the formation of voids in the reaction medium and to prevent fracture of the reaction medium.

4. The reaction vessel of claim 3 wherein the reaction medium includes an electrolyte.

5. The reaction vessel of claim 3 wherein the reaction medium is a granular salt susceptible to volume changes by osmotic reaction with a buffer solution.

6. The reaction vessel of claim 3 wherein the resilient membranes have an unhydrated thickness of approximately 0.090" and a hydrated thickness of approximately 0.150".

7. The reaction vessel of claim 6 wherein the manifold chambers include a plurality of fins directed radially outward from the fluid inlet and fluid outlet to define the fluid pathways and to position the resilient membranes in a spaced relationship from the fluid inlet and fluid outlet and wherein the resilient membranes are positioned in contact with the reaction medium.

8. The reaction vessel of claim 7 wherein the fins and the reaction medium have a minimum separation distance of approximately 0.110" so that portions of the resilient membranes are in contact with both the fins and the reaction medium, wherein the resilient membranes are slightly compressed when the reaction medium is hydrated.

9. A vertical reaction vessel having a uniform fluid flow design, comprising:
   a body defining a reaction medium receptacle having a receptacle cross-sectional area;
   a reaction medium is the receptacle;
   a fluid inlet communicating with the reaction medium receptacle and having an inlet cross-sectional area substantially smaller than the receptacle cross-sectional area;
   a manifold chamber adjacent to the fluid inlet having a manifold cross-sectional area substantially equal to the receptacle cross-sectional area to provide a plurality of fluid passageways from the fluid inlet across the receptacle cross-sectional area; and fluid-permeable back pressures means, located between the manifold chamber and the reaction medium, for gently compensating for volumetric changes of said reaction medium and for evenly distributing fluid through the fluid passageway substantially throughout the manifold cross-sectional area to encourage substantially uniform fluid flow through the reaction medium.

10. The reaction vessel of claim 9 wherein the manifold chamber includes a plurality of fins extending radially outward from the fluid inlet to position the fluid back pressure means in a spaced relationship from the fluid inlet so as to define the fluid pathways.

11. The reaction vessel of claim 10 wherein the fluid-permeable back pressure means includes a resilient membrane which expands when hydrated and wherein the reaction medium is relatively fragile and has a volume which expands and contracts according to the ionic strength of a buffer solution introduced into the fluid inlet, whereby the volume of the resilient membrane changes to complement volume changes of the reaction medium to prevent the formation of voids in the reaction medium and to prevent fracture of the reaction medium.

12. The reaction vessel of claim 11 wherein the reaction medium includes an electrolyte.

13. The reaction vessel of claim 11 wherein the reaction medium is a granular salt susceptible to volume changes by osmotic reaction with a buffer solution.

14. The reaction vessel of claim 11 wherein the resilient membrane has an unhydrated thickness of approximately 0.090" and a hydrated thickness of approximately 0.150".

15. The reaction vessel of claim 14 wherein the manifold chamber includes a plurality of fins extending radially outward from the fluid inlet to position the resilient membrane in a spaced relationship from the fluid inlet so as to define the fluid pathways and wherein the resilient membrane is positioned in contact with the reaction medium.

16. The reaction vessel of claim 15 wherein the fins and the reaction medium have a minimum separation distance of approximately 0.110" so that portions of the resilient membrane in contact with both the fins and the reaction medium are slightly compressed when the reaction medium is hydrated.

17. A method for reacting a solution with a reaction medium, and for compensating for volumetric changes in a reaction medium which is relatively fragile and has a volume which expands and contracts when exposed to a buffer solution having an ionic concentration, comprising the steps of:
introducing fluid into a fluid inlet of a reaction vessel having a reaction medium of substantially constant cross-sectional area and a fluid distribution chamber between the fluid inlet and the reaction medium having a cross-sectional area substantially equal to the reaction medium cross-sectional area;
distributing the introduced fluid throughout substantially the entire cross-sectional area of the fluid distribution chamber;
providing a resilient membrane between the fluid distribution chamber and the reaction medium, wherein the resilient membrane is of the type which expands when hydrated and wherein the reaction medium is relatively fragile and has a volume which expands and contracts according to the ionic strength of a buffer solution introduced into the fluid inlet;
expanding the resilient membrane when the reaction medium contracts to prevent the formation of voids in the reaction medium;
contracting the resilient membrane when the reaction medium expands to prevent fracture of the reaction medium; and 18. A vertical reaction vessel having a uniform fluid flow design for use with a reaction medium which compensates for volumetric changes in a reaction medium which is relatively fragile and has a volume which expands and contracts when exposed to a buffer solution having an ionic concentration, comprising:
a body defining a reaction medium receptacle having a receptacle cross-sectional area;
a reaction medium in the receptacle;
a fluid inlet communicating with the reaction medium receptacle and having an inlet cross-sectional area substantially smaller than the receptacle cross-sectional area;
low resistance horizontal flow means, adjacent to the fluid inlet, for causing a first resistance to fluid flow in a horizontal direction from the fluid inlet substantially throughout the entire cross-sectional area of the reaction medium receptacle;
high resistance vertical flow means, adjacent to the low resistance horizontal flow means, for causing a second resistance to fluid flow in a vertical direction toward the reaction medium which is greater than the first resistance to fluid flow, whereby fluid is distributed throughout substantially the entire cross-sectional area of the reaction medium receptacle prior to entering the reaction meadium; and
volume compensating means for compensating for volumetric changes in the reaction medium due to the ionic concentration of a buffer solution.

19. A method for purifying a reaction solution containing desirable conjugated antibody and undesirable ionic material, comprising the steps of:
introducing the reaction solution into a fluid inlet having an inlet cross-sectional area;
distributing the fluid radially from the fluid inlet through a fluid distribution manifold having a manifold cross-sectional area substantially larger than the inlet cross-sectional area;
providing a resilient, fluid-permeable back pressure device adjacent to the fluid distribution manifold constructed of a material which gently expands and contracts sufficient to accomodate volumetric changes of the low-exchange material to prevent fracture of the low-exchange material and the formation of voids in the low-exchange material; and
directing the fluid through the fluid-permeable back pressure device and into an ion-exchange material contained in an ion-exchange chamber having a chamber cross-sectional area substantially equal to the manifold cross-sectional area.

* * * * *

UNITED STATES PATENT AND TRADEMARK OFFICE
CERTIFICATE OF CORRECTION

PATENT NO. : 4,871,463

DATED : October 3, 1989

INVENTOR(S) : Michael A. Taylor; Timothy Rogler-Brown

It is certified that error appears in the above-identified patent and that said Letters Patent is hereby corrected as shown below:

In claim 9, column 6, line 59, delete "is" and substitute therefor --in--.

In claim 17, column 8, line 12, following "and" insert --directing the introduced fluid into the reaction medium--.

In claim 18, column 8, line 38, delete "meadium" and substitute therefor --medium--.

Signed and Sealed this

Fourth Day of September, 1990

Attest:

HARRY F. MANBECK, JR.

Attesting Officer

Commissioner of Patents and Trademarks